United States Patent
Kreindel

(10) Patent No.: US 8,244,369 B2
(45) Date of Patent: Aug. 14, 2012

(54) DEVICE AND METHOD FOR TREATING SKIN WITH TEMPERATURE CONTROL

(75) Inventor: Michael Kreindel, Zichron Ya'acov (IL)

(73) Assignee: Syneron Medical Ltd., Yokneam Illit (IL)

(*) Notice: Subject to any disclaimer, the term of this patent is extended or adjusted under 35 U.S.C. 154(b) by 1434 days.

(21) Appl. No.: 11/808,567

(22) Filed: Jun. 11, 2007

(65) Prior Publication Data

US 2008/0004678 A1    Jan. 3, 2008

Related U.S. Application Data

(63) Continuation-in-part of application No. 11/044,610, filed on Jan. 28, 2005, now Pat. No. 7,643,883.

(51) Int. Cl.
*A61F 2/00* (2006.01)

(52) U.S. Cl. ............. 607/101; 607/89; 607/99; 607/102

(58) Field of Classification Search ............. 606/27–50; 607/88–89, 96
See application file for complete search history.

(56) References Cited

U.S. PATENT DOCUMENTS

| | | | |
|---|---|---|---|
| 5,233,515 A * | 8/1993 | Cosman | 600/549 |
| 5,755,753 A | 5/1998 | Knowlton | |
| 5,919,219 A | 7/1999 | Knowlton | |
| 5,938,657 A | 8/1999 | Assa et al. | |
| 6,002,963 A * | 12/1999 | Mouchawar et al. | 607/18 |
| 6,091,995 A | 7/2000 | Ingle et al. | |
| 6,241,753 B1 | 6/2001 | Knowlton | |
| 6,413,255 B1 | 7/2002 | Stern | |
| 6,662,054 B2 * | 12/2003 | Kreindel et al. | 607/101 |
| 6,702,808 B1 | 3/2004 | Kreindel | |
| 6,749,624 B2 | 6/2004 | Knowlton | |
| 6,749,626 B1 | 6/2004 | Bhat et al. | |
| 6,749,828 B1 | 6/2004 | Fukunaga | |
| 6,766,202 B2 | 7/2004 | Underwood et al. | |
| 7,204,832 B2 * | 4/2007 | Altshuler et al. | 606/9 |
| 7,276,058 B2 * | 10/2007 | Altshuler et al. | 606/9 |
| 7,278,991 B2 | 10/2007 | Morris et al. | |
| 7,367,974 B2 * | 5/2008 | Haemmerich et al. | 606/41 |
| 7,762,964 B2 * | 7/2010 | Slatkine | 601/7 |
| 2002/0002392 A1 | 1/2002 | Bernabei | |

(Continued)

FOREIGN PATENT DOCUMENTS

CN    1879573 A    12/2006

(Continued)

*Primary Examiner* — Roy Gibson
(74) *Attorney, Agent, or Firm* — Susanne M. Hopkins; William L. Klima; Ari G. Zytcer

(57) ABSTRACT

A method and system for heating a skin area surface of an individual from an initial temperature to a treatment temperature in a treatment time period exceeding 0.5 sec, where the treatment temperature is in the range of 40°-60° C. An RF generator provides a continuous wave RF voltage energy or a quasi-continuous wave RF voltage across first and second electrode, where at least the first electrode is associated with an applicator that is displaced over the skin surface. The system further includes a skin temperature measuring device or an applicator displacement speed measuring device; and a CPU that monitors a skin temperature or an applicator displacement speed. The CPU turns off the RF energy when the skin temperature is above a predetermined temperature or the displacement speed of the applicator is below a predetermined speed, in order to prevent overheating of the skin.

32 Claims, 3 Drawing Sheets

U.S. PATENT DOCUMENTS

| | | |
|---|---|---|
| 2002/0043520 A1 | 4/2002 | Bernabei |
| 2003/0032950 A1 | 2/2003 | Altshuler et al. |
| 2003/0073989 A1* | 4/2003 | Hoey et al. ............... 606/34 |
| 2005/0015125 A1 | 1/2005 | Mioduski et al. |
| 2005/0131288 A1 | 6/2005 | Turner et al. |
| 2005/0209193 A1 | 9/2005 | Keller |
| 2006/0173518 A1 | 8/2006 | Kreindel |

FOREIGN PATENT DOCUMENTS

| | | |
|---|---|---|
| WO | 02/094116 A1 | 11/2002 |

* cited by examiner

DEVICE AND METHOD FOR TREATING SKIN WITH TEMPERATURE CONTROL

This application is a CIP of U.S. patent application Ser. No. 11/044,610 filed Jan. 28, 2005 now U.S. Pat. No. 7,643,883, the contents of which are hereby incorporated by reference in their entirety.

FIELD OF THE INVENTION

This invention relates to methods and devices for treating skin.

BACKGROUND OF THE INVENTION

There are many medical and cosmetic treatments of skin that utilize heating a region of skin to be treated. Among these are hair removal, treatment of vascular lesions and skin rejuvenation. In these treatments, a volume of skin tissue to be treated is heated to a temperature that sufficiently high to achieve a desired effect, which is typically in the range of 45-60° C. One method that has been used for heating the epidermal and dermal layers of the skin is pulsed radiofrequency (RF) energy. In this method, electrodes are applied to the skin and an RF voltage pulse is applied across the electrodes. The properties of the voltage pulse are selected so as to generate an RF current pulse in the tissue to be treated that heats the tissue to the required temperature. For example, U.S. Pat. No. 6,749,626 discloses use of pulsed RF energy for inducing collagen formation in the dermis.

When an RF current pulse is used to heat a volume of tissue, the temperature of the tissue volume rises from body temperature to the required temperature within the duration of the pulse, which is typically of the order of 100 msec. The temperature of the tissue volume thus rises vary rapidly. Since the final temperature will actually depend on the electrical properties of the tissue volume which vary from individual to individual, the rapid rise in temperature of the tissue volume limits control of the tissue heating. Moreover, the rapid rise in temperature prevents the user from stopping the treatment should the tissue volume become overheated. Thus, using an RF pulse to heat the skin carries a risk of overheating the skin which could result in permanent scarring or other damage to the skin surface. Such damage to the skin includes, for example, a first degree or higher burn, blisters, or blood coagulation.

SUMMARY OF THE INVENTION

The present invention provides a method and system for heating a sub-dermal tissue volume. In accordance with the invention an RF current is generated in a tissue volume to be treated that raises the temperature of the tissue volume to a desired temperature above its initial temperature in a period of time that exceeds 0.5 sec. The slow rise in temperature allows the user to control the skin temperature and to avoid overheating of the skin. The invention is particularly useful for skin treatments requiring the tissue volume to be heated to a temperature in the range of 45° C. to 60° C. Such treatments include, for example, skin rejuvenation, collagen remodeling and contraction, skin tightening, wrinkle treatment, subcutaneous tissue treatment, cellulite treatment, pore size reduction, skin texture and tone improvement, acne treatment and hair removal.

In one embodiment of the invention, a pair of RF electrodes is applied to the skin surface, and an RF energy pulse is applied to the skin surface having a duration and power selected so as to heat the skin surface to a predetermined temperature within an amount of time exceeding 0.5 sec. For example, an RF energy pulse having a power range of 1-10 Watts could be used. In this case application of RF energy would heat the tissue volume to a temperature in the range of 40°-60° C. within 0.5-10 sec. The electrodes could be positioned at a first location in a skin region to be treated and the RF energy pulse applied to the first location. The electrode pair could then be repositioned on the skin surface at another location in the region to be treated and the procedure repeated. In another embodiment of the invention, continuous wave (CW) RF energy is applied to the skin surface and by a pair of electrodes which is displaced over the skin surface at a displacement speed that sequentially heats a tissue volume adjacent to the electrodes to the predetermined temperature in a time that exceeds 0.5 sec. For example, CW RF energy having a power range of 2-10 Watts could be used. In this case, a displacement speed of about 0.5-1.0 cm/sec would heat the tissue volume to a temperature in the range of 45°-60° C. in a time that exceeds 0.5 sec. Quasi-CW RF energy may also be used in which a train of RF pulses is applied to the skin surface, where the train has a frequency and the pulses have durations and powers, so as to heat the tissue volume to be treated to a predetermined temperature in a period of time that exceeds 0.5 sec.

The system of the invention comprises two or more RF electrodes and an RF generator configured to apply an RF voltage across at least a pair of electrodes, where the RF voltage has a power selected to heat a tissue volume to a predetermined temperature in a time period that exceeds 0.5 sec., when an electrode pair is applied to the skin surface over the tissue volume. The RF generator may be configured to deliver a pulse of RF energy having a duration exceeding 0.5 sec. Alternatively, the RF generator could be configured to deliver CW or quasi-CW RF energy to the electrodes, in which case, the electrodes are displaced over the skin surface during delivery of the RF energy. In a preferred embodiment of the system, a pair of RF electrodes is included in a hand held applicator. A user treating his own skin with the system of the invention may simply displace the applicator over the skin surface in the region to be treated at a speed at which the user feels that the skin is heated but not to an extent that causes pain to the user.

The slow heating of the skin volume by the method and system of the invention permits greater control of the tissue heating, and thus reduces the risk of overheating, and hence damaging, the tissue.

Damage to the skin may include, for example, a first degree or higher burn, blisters, or blood coagulation. The appropriate displacement speed of the applicator over the skin is thus a function of the RF power. As the RF power increases, the movement of the applicator over the skin surface should be faster in order to avoid skin damage due to overheating of the skin.

The system includes a control mechanism that turns off or reduces the RF energy when a condition indicative of skin overheating occurs, in order to prevent overheating of the skin that could otherwise occur if the applicator were to be displaced over the skin by the user too slowly or not at all during delivery of RF energy to the skin. In one embodiment, the control system includes a temperature sensor, such as a thermistor or thermocouple that measures the skin temperature during delivery of RF energy. The skin temperature is monitored by the system which automatically turns off the RF energy when the skin temperature exceeds a predetermined threshold.

In another embodiment, the system includes a motion detector that continuously monitors the movement of the applicator over the skin. An optical or mechanical device can be used for the motion detection. An accelerometer may also be used for motion detection. In this embodiment, the system turns off the RF energy when the speed of the applicator is below a predetermined threshold or when the applicator is applied to the skin and not moved for a period of time which is longer than a predetermined time period. In a preferred embodiment, the control mechanism involves measuring the electrical impedance of the skin between a pair of RF electrodes. A processor continuously calculates the skin temperature from the impedance measurements and turns off the RF energy when the calculated temperature is above a predetermined threshold.

Thus, in one of its aspects, the invention provides a system for heating a tissue volume under the skin surface of an individual from an initial temperature to a treatment temperature in a treatment time period exceeding 0.5 sec, the treatment temperature being in the range of 40°-60° C., comprising:
- (a) an applicator;
- (b) a first electrode and a second electrode, at least the first electrode being associated with the applicator;
- (c) an RF generator configured to provide a continuous wave RF voltage energy or a quasi-continuous wave RF voltage across the first and second electrodes;
- (d) A skin temperature measuring device or an applicator motion detector device; and
- (e) a CPU configured to monitor a skin temperature or an applicator displacement speed and to turn off or reduce the RF energy when the skin temperature is above a predetermined temperature or the displacement speed of the applicator is below a predetermined speed.

In another of its aspects, the invention provides a method for heating a tissue volume under the skin surface of an individual from an initial temperature to a treatment temperature in a treatment time period exceeding 0.5 sec, the treatment temperature being in the range of 40°-60° C., comprising:
- (a) providing a continuous wave RF voltage energy or a quasi-continuous wave RF voltage across a first electrode and a second electrode, at least one of the first electrode and the second electrode being associated with an applicator;
- (b) displacing the applicator over the skin surface;
- (c) monitoring a skin temperature or an applicator motion
- (d) turning off or reducing the RF energy when the skin temperature is above a predetermined temperature or the displacement speed of the applicator is below a predetermined speed.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
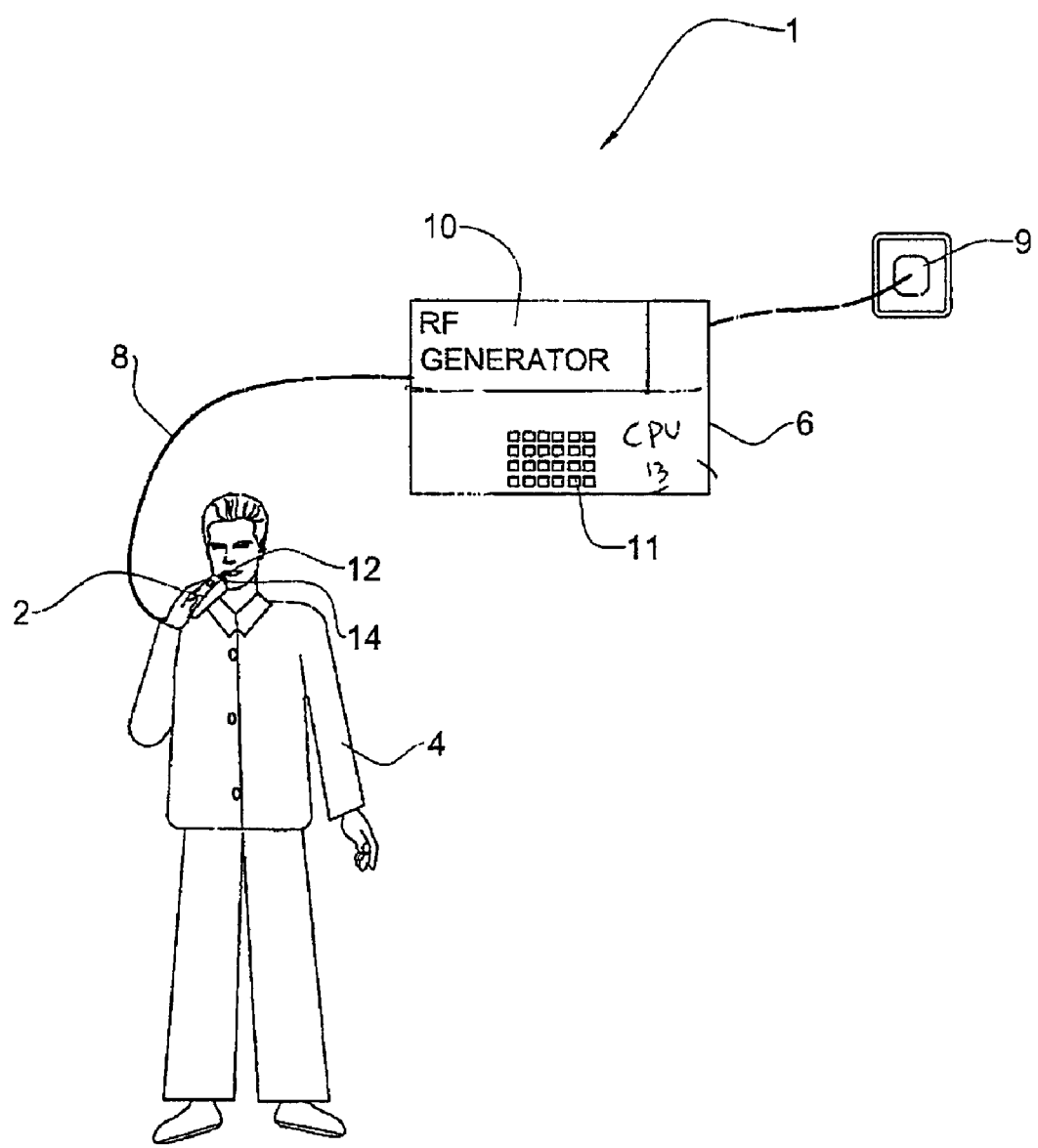
FIG. 1 shows a system for treating skin in accordance with one embodiment of the invention.

FIG. 1 shows a system 1 for treating skin in accordance with one embodiment of the invention. The system 1 includes a hand held applicator 2 that is used to apply RF energy to the skin of an individual 4. The applicator 2 is connected to a control unit 6 via a harness 8. The control unit 6 includes an RF generator 10 that generates a continuous wave or quasi-continuous RF voltage across a pair of electrodes 12 and 14 in the applicator 2. The control unit 10 also includes a CPU 13 and an input device such as a key pad 11 for inputting to the CPU 13 the wavelength and amplitude of the RF voltage generated by the RF generator 10 as required in any particular skin treatment. The RF generator is connected to the electrodes 12 and 14 by a pair of wires in the harness 8. The system 1 may be plugged into a wall electrical socket 9, as shown in FIG. 1 or use batteries (not shown) that are preferably rechargeable.

Figure 2:
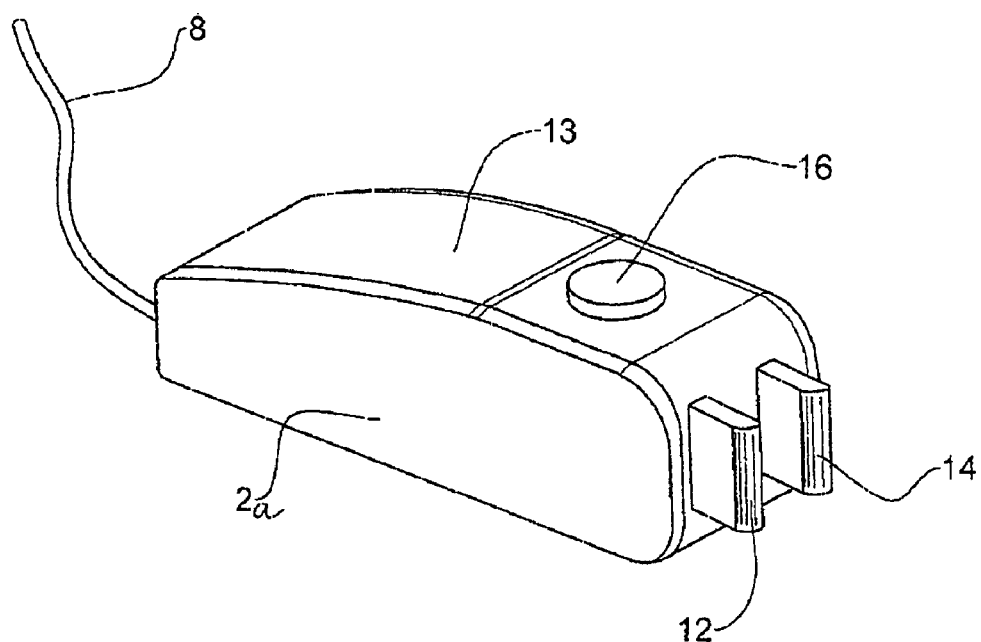
FIG. 2 shows an applicator for use in the system of FIG. 1.
Figure 3:
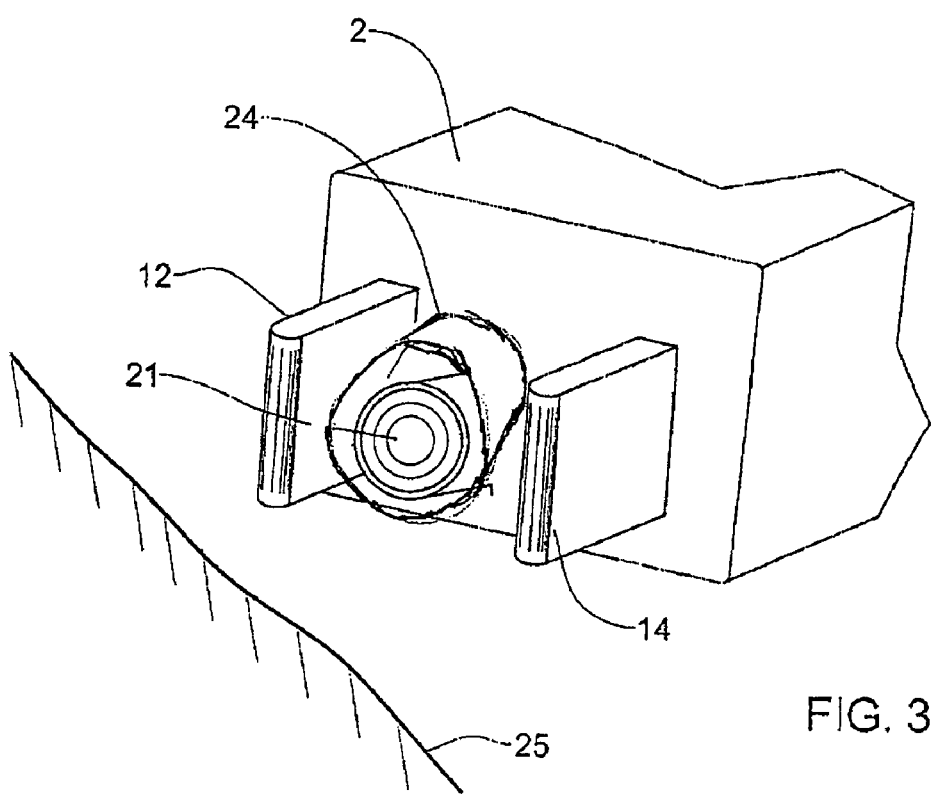
FIG. 3 shows the electrodes of the applicator of FIG. 2.

FIGS. 2 and 3 show an applicator 2a in accordance with one embodiment of the applicator 2. The applicator 2a contains a push-button on-off switch 16. The switch 16 is spring biased in an open position, so that no voltage is applied to the electrodes 12 and 14 when the switch 16 is released. When the applicator 2 is held by a user, as shown in FIG. 1, the switch 16 is depressed and a continuous or quasi-continuous wave RF voltage (train of repetitive pulses) is applied between the electrodes 12 and 14. The electrodes 12 and 14 preferably have rounded edges in order to avoid hot spots on the skin surface in the vicinity of the edges of the electrodes. Rounded electrodes also allow smooth moving of the applicator over the skin surface.

The applicator 2a preferably, though not necessarily, includes a light source 21 which is located between the electrodes 12 and 14 that generates optical energy that is directed to the skin 25 surface by a reflector 24. Optical energy directed to the skin surface from the light source 21 is used to specifically heat pigmented targets at the skin surface. Such skin targets include vascular lesions, varicose veins, acne, and mole marks. The optical energy may have a single wavelength or several wavelengths. The wavelengths are selected to be optimal for the color of the contrasted component of the target, and are typically in the range of 400 to 1800 nm. A filament lamp or gas filled lamp can be used as the light source 21. Light from a laser or LED also can be used for skin irradiation.

In use, the applicator 2 is held by the user and the electrodes 12 and 14 are applied to the skin. The switch 16 is then depressed so as to deliver a continuous wave RF current to a section 17 of the skin between the electrodes 12 and 14. The applicator 2 is displaced over the skin in a skin region 15 to be treated so as to heat the skin region to a temperature that produces the desired treatment of the skin.

When the applicator 2a is used, the CPU 13 continuously monitors the electrical impedance of the skin between the electrodes 12 and 14. Increasing skin temperature leads to a change in impedance, monitoring the skin impedance allows the temperature in the skin between the electrodes to be followed, as is known in the art. The CPU 13 is configured to continuously calculate a skin temperature from the impedance measurements and to turn off the RF energy when the calculated skin temperature is above a predetermined threshold.

Figure 4:
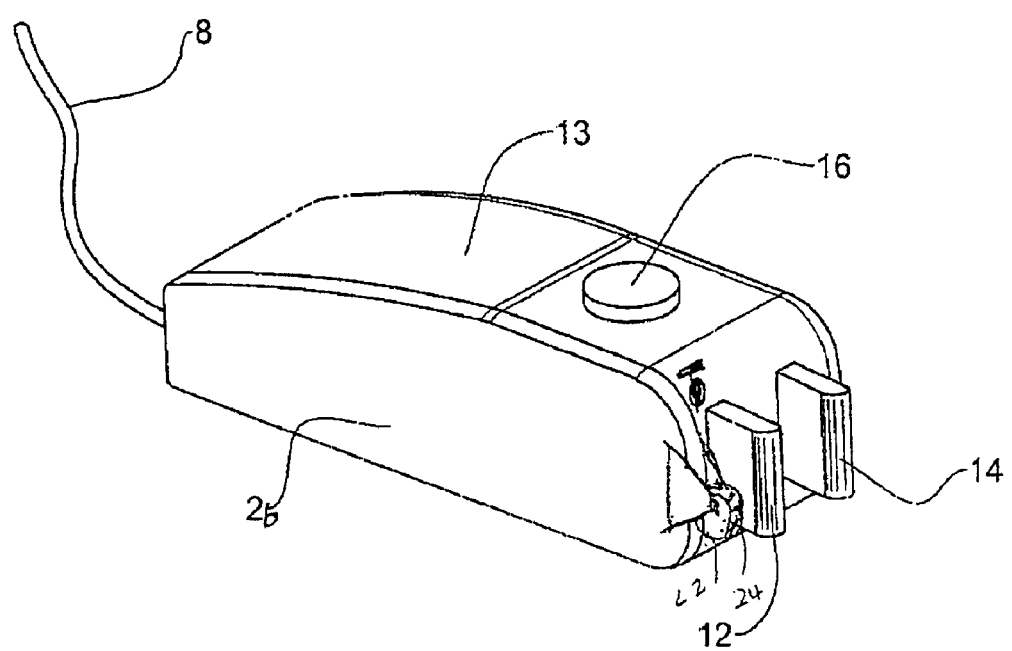
FIG. 4 shows another applicator for use in the system of FIG. 1.

FIG. 4 shows an applicator 2b in accordance with another embodiment of the applicator 2. The applicator 2b has several elements in common with the applicator 2a shown in FIGS. 2 and 3, and similar elements are indicated by the same reference numeral in FIGS. 2, 3, and 4 without further comment.

The applicator 2b has roller 20 adjacent to the electrode pair that is positioned and dimensioned to contact the skin surface and to roll over the skin surface as the applicator is displaced over the skin surface. The roller 20 has a plurality of evenly spaced radial markers 22 on its edge 24. The edge 24 is illuminated by light from a laser 26. Light reflected from the edge 24 is detected by a photo cell 28 that generates an electric signal indicative of the intensity of the reflected light. Due to the presence of the radial markers 22 the intensity of the reflected light, and hence the intensity of the electric signal, varies cyclically as the roller rolls over the skin surface. The electrical signal is continuously monitored by the CPU 13 which is configured to calculate a displacement speed of the applicator 2b over the skin surface from the periodicity of the electrical signal which is proportional to the displacement speed of the applicator. The CPU 13 in this embodiment is configured to turn off the RF energy when the displacement speed is below a predetermined value.

When the CPU determines that the skin temperature is above the predetermined temperature, the processor may generate a sensible signal, such as sounding an alarm 15 at a pitch indicating to the user that the displacement speed is too low and that the RF energy has been turned off. Similarly, if the CPU 13 determines that the skin temperature is below a second predetermined value that is required to produce the desired skin treatment (for example, 45° C. to 60° C., which maybe input to the CPU 13 prior to the treatment), the processor may generate a sensible signal, such as sounding the alarm 15 at another pitch indicating to the user that the displacement speed should be increased.

The displacement velocity of the applicator 2 over the skin is determined so that the skin section between the electrodes is heated to a temperature that produces the desired skin treatment, but does not damage the skin. The desired displacement speed can be determined, for example, using the equation $$V = \frac{P}{L d\, c\rho \Delta T},$$

where P is the power of the continuous RF current, L is the spacing of the electrodes, d is the penetration depth of the RF energy, c is the specific heat of the treated tissue, $\rho$ is the mass density of the tissue, and $\Delta T$ is the required temperature increase. Thus, for example, if the RF power is P=5 W, the spacing of the electrodes is L=1 cm, the RF penetration depth is d=0.25 cm, c$\rho$=4 J/cm$^3$/°K. and $\Delta T$=10° C., the applicator displacement speed should be about 0.5 cm/sec. in order to achieve the desired heating in amount of time in slightly more than 0.5 sec. If a mono-polar electrode system is used, the power should be lower to avoid damage to sub-dermal tissue.

The system 1 may be used with the following exemplary parameter values:

An RF power in the range of 2-10 W.
An energy delivery mode that is CW or Quasi-CW.
An RF frequency in the range of 0.2-10 MHz.
An optical energy spectrum in the range of 400-1800 nm.
Optical energy power in the range of 1 to 20 W/cm$^2$.

The invention claimed is:

1. A method for heating a tissue volume under the skin surface of an individual from an initial temperature to a treatment temperature in the range of 40 degrees to 60 degrees C, comprising:
   (a) providing a continuous or a quasi-continuous wave RF energy across a first electrode and a second electrode, at least one of the electrodes being associated with an applicator;
   (b) heating the tissue volume in a treatment time period exceeding 0.5 sec;
   (c) displacing the applicator over the skin surface;
   (d) monitoring a skin temperature;
   (e) monitoring applicator displacement speed employing a motion sensor; and
   (f) turning off or reducing the RF energy when the skin temperature is above a predetermined temperature or the displacement speed of the applicator is below a predetermined speed.

2. The method according to claim 1 wherein monitoring the skin temperature using an electronic or optical device.

3. The method according to claim 1 wherein said monitoring skin temperature comprises measuring skin impedance and calculating skin temperature based on said measured skin impedance.

4. The method according to claim 1 wherein the applicator motion is measured using a roller rolling over the skin surface when the applicator is displaced over the skin surface.

5. The method according to claim 1 wherein the applicator motion is measured by measuring the acceleration of the applicator.

6. The method according to claim 1 wherein the applicator motion is measured using an optical device.

7. The method according to claim 1 wherein two or more electrodes are associated with the applicator.

8. The method according to claim 1 wherein the power of said RF energy wave is in the range of 1-50 W.

9. The method according to claim 1 wherein the RF voltage has a frequency in the range of 0.2-50 MHz.

10. The method according to claim 1 further comprising directing optical energy to the skin surface.

11. The method according to claim 10 wherein at least part of the optical energy has a spectrum in the range of 400-1800 nm.

12. The method according to claim 11 wherein the sensible signal is sounding an alarm at a first pitch.

13. The method according to claim 10 wherein the optical energy has an energy power density in the range of 0.01 to 10 W/cm$^2$.

14. The method according to claim 10 wherein a source of said optical energy is at least one selected from the group consisting of an incandescent lamp, a gas filled lamp, a LED and a laser.

15. The method according to claim 14 wherein the sensible signal is sounding an alarm at a second pitch or a visible signal.

16. The method according to claim 1 further comprising determining a wherein said monitoring skin temperature comprises measuring skin impedance and calculating heat distribution in the skin based upon one or more of the impedance measurements.

17. The method according to claim 1 further comprising generating a sensible signal if the skin temperature is below a predetermined temperature.

18. The method according to claim 1 further comprising generating a sensible signal if the skin temperature is above a predetermined temperature.

19. A method for heating a tissue volume under the skin surface of an individual from an initial temperature to a treatment temperature in the range of 40 degrees to 60 degrees C., comprising:
   (a) providing a continuous wave or a quasi-continuous wave RF energy across a first electrode and a second electrode, at least one of the electrodes being associated with an applicator;
   (b) heating said in a treatment time period exceeding 0.5 sec;
   (c) displacing the applicator over the skin surface;

(d) monitoring a skin temperature;
(e) monitoring applicator motion by using at least one from the group consisting of:
   a roller rolling over the skin surface when the applicator is displaced over the skin surface;
   measuring the acceleration of the applicator; and
   an optical device; and
(f) turning off or reducing the RF energy when the skin temperature is above a predetermined temperature or the displacement speed of the applicator is below a predetermined speed.

20. The method according to claim 19, wherein said monitoring skin temperature comprises measuring skin impedance and calculating skin temperature based on said measured skin impedance.

21. The method according to claim 19, wherein two or more electrodes are associated with the applicator.

22. The method according to claim 19, wherein the power of said energy wave is in the range of 1-50 W.

23. The method according to claim 19, wherein the RF voltage has a frequency in the range of 0.2-50 MHz.

24. The method according to claim 19, further comprising directing optical energy to the skin surface.

25. The method according to claim 24, wherein at least part of the optical energy has a spectrum in the range of 400-1800 nm.

26. The method according to claim 24, wherein the optical energy has an energy power density in the range of 0.01 to 10 W/cm2.

27. The method according to claim 24, wherein a source of said optical energy is at least one selected from the group consisting of an incandescent lamp, a gas filled lamp, a LED and a laser.

28. The method according to claim 19, wherein said monitoring skin temperature comprises measuring skin impedance and calculating heat distribution in the skin based upon one or more of the impedance measurements.

29. The method according to claim 19, further comprising generating a sensible signal if the skin temperature is below a predetermined temperature.

30. The method according to claim 29, wherein the sensible signal is sounding an alarm at a first pitch.

31. The method according to claim 19, further comprising generating a sensible signal if the skin temperature is above a predetermined temperature.

32. The method according to claim 31, wherein the sensible signal is sounding an alarm at a second pitch or a visible signal.

* * * * *